(12) United States Patent
Fell et al.

(10) Patent No.: US 9,012,716 B2
(45) Date of Patent: Apr. 21, 2015

(54) ABSORBENT ARTICLES WITH IMPROVED ODOR CONTROL

(75) Inventors: David Arthur Fell, Neenah, WI (US); Megan Lan, Choluteca (HN); William Anthony Georger, Appleton, WI (US); Kelly Davis Arehart, Roswell, GA (US); Bao Trong Do, Decatur, GA (US); Stephanie Michelle Martin, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 72 days.

(21) Appl. No.: 12/826,143

(22) Filed: Jun. 29, 2010

(65) Prior Publication Data

US 2010/0292661 A1     Nov. 18, 2010

Related U.S. Application Data

(62) Division of application No. 11/263,598, filed on Oct. 31, 2005, now Pat. No. 7,745,685.

(51) Int. Cl.

| | |
|---|---|
| *A61F 13/15* | (2006.01) |
| *A61F 13/20* | (2006.01) |
| *A61L 15/46* | (2006.01) |
| *A61F 13/53* | (2006.01) |

(Continued)

(52) U.S. Cl.
CPC ............ *A61L 15/46* (2013.01); *A61F 13/15658* (2013.01); *A61F 13/53* (2013.01); *A61F 13/8405* (2013.01); *A61F 2013/15943* (2013.01); *A61F 2013/530489* (2013.01); *A61F 2013/530671* (2013.01); *A61F 2013/8408* (2013.01); *A61F 2013/8426* (2013.01); *A61F 2013/8435* (2013.01); *A61F 2013/8447* (2013.01); *A61F 2013/8461* (2013.01); *A61L 9/014* (2013.01); *A61L 15/18* (2013.01); *A61L 2300/10* (2013.01); *A61L 2300/216* (2013.01); *A61L 2300/606* (2013.01)

(58) Field of Classification Search
USPC .......................................... 604/359–360, 367
See application file for complete search history.

(56) References Cited

U.S. PATENT DOCUMENTS

| | | |
|---|---|---|
| 3,647,415 A | 3/1972 | Yano et al. |
| 3,802,817 A | 4/1974 | Matsuki et al. |

(Continued)

FOREIGN PATENT DOCUMENTS

| | | |
|---|---|---|
| DE | 10017446 A1 | 11/2001 |
| EP | 0348978 A2 | 1/1990 |

(Continued)

OTHER PUBLICATIONS

English Abstract for JP 2006659, Jan. 10, 1990.

(Continued)

*Primary Examiner* — Michele M Kidwell
(74) *Attorney, Agent, or Firm* — Dority & Manning, P.A.

(57) ABSTRACT

A technique for incorporating odor control agent particles into an absorbent article is provided. More specifically, the odor control particles are "homogenously" distributed (e.g., in a substantially uniform manner) within an airformed fiber matrix of an absorbent core of an absorbent article. An absorbent core containing such a homogeneously distributed odor control particles may possess a greater surface area for contacting malodorous compounds, thereby increasing the likelihood of odor reduction.

16 Claims, 2 Drawing Sheets

(51) Int. Cl.
   *A61F 13/84* (2006.01)
   *A61L 9/014* (2006.01)
   *A61L 15/18* (2006.01)

(56) References Cited

U.S. PATENT DOCUMENTS

| | | | |
|---|---|---|---|
| 4,118,832 A | 10/1978 | Addy et al. | |
| 4,285,343 A | 8/1981 | McNair | |
| 4,375,448 A | 3/1983 | Appel et al. | |
| 4,488,969 A | 12/1984 | Hou | |
| 4,572,440 A | 2/1986 | Tao | |
| 4,604,313 A | 8/1986 | McFarland et al. | |
| 4,608,047 A | 8/1986 | Mattingly | |
| 4,650,479 A | 3/1987 | Insley | |
| 4,666,647 A | 5/1987 | Enloe et al. | |
| 4,687,478 A | 8/1987 | Van Tilburg | |
| 4,704,116 A | 11/1987 | Enloe | |
| 4,761,258 A | 8/1988 | Enloe | |
| 4,765,780 A | 8/1988 | Angstadt | |
| 4,798,603 A | 1/1989 | Meyer et al. | |
| 4,886,512 A | 12/1989 | Damico et al. | |
| 4,927,582 A | 5/1990 | Bryson | |
| 4,950,264 A | 8/1990 | Osborn, III | |
| 5,009,653 A | 4/1991 | Osborn, III | |
| 5,085,654 A | 2/1992 | Buell | |
| 5,176,668 A | 1/1993 | Bernardin | |
| 5,176,672 A | 1/1993 | Bruemmer et al. | |
| 5,190,563 A | 3/1993 | Herron et al. | |
| 5,192,606 A | 3/1993 | Proxmire et al. | |
| 5,197,959 A | 3/1993 | Buell | |
| 5,227,107 A | 7/1993 | Dickenson et al. | |
| 5,267,992 A | 12/1993 | Van Tilburg | |
| 5,284,703 A | 2/1994 | Everhart et al. | |
| 5,308,346 A | 5/1994 | Sneller et al. | |
| 5,308,896 A | 5/1994 | Hansen et al. | |
| 5,342,342 A | 8/1994 | Kitaoka | |
| 5,350,370 A | 9/1994 | Jackson et al. | |
| 5,352,480 A * | 10/1994 | Hansen et al. | 427/202 |
| 5,407,600 A | 4/1995 | Ando et al. | |
| 5,427,844 A | 6/1995 | Murai et al. | |
| 5,429,628 A | 7/1995 | Trinh et al. | |
| 5,432,000 A | 7/1995 | Young, Sr. et al. | |
| 5,447,977 A * | 9/1995 | Hansen et al. | 524/13 |
| 5,486,166 A | 1/1996 | Bishop et al. | |
| 5,490,846 A | 2/1996 | Ellis et al. | |
| 5,509,914 A | 4/1996 | Osborn, III | |
| 5,509,915 A | 4/1996 | Hanson et al. | |
| 5,543,215 A | 8/1996 | Hansen et al. | |
| 5,558,659 A | 9/1996 | Sherrod et al. | |
| 5,569,234 A | 10/1996 | Buell et al. | |
| 5,609,727 A | 3/1997 | Hansen et al. | |
| 5,634,916 A | 6/1997 | Lavon et al. | |
| 5,649,916 A | 7/1997 | DiPalma et al. | |
| 5,702,378 A | 12/1997 | Widlund et al. | |
| 5,716,349 A | 2/1998 | Taylor et al. | |
| 5,779,857 A | 7/1998 | Norlander | |
| 5,837,627 A | 11/1998 | Halabisky et al. | |
| 5,909,718 A | 6/1999 | Sheehan | |
| 6,024,822 A | 2/2000 | Alper et al. | |
| 6,110,158 A | 8/2000 | Kielpikowski | |
| 6,149,934 A | 11/2000 | Krzysik et al. | |
| 6,229,062 B1 | 5/2001 | Mandell et al. | |
| 6,330,735 B1 | 12/2001 | Hahn et al. | |
| 6,369,290 B1 | 4/2002 | Glaug et al. | |
| 6,376,741 B1 | 4/2002 | Guarracino et al. | |
| 6,425,979 B1 | 7/2002 | Hansen et al. | |
| 6,511,465 B1 | 1/2003 | Freiburger et al. | |
| 6,521,339 B1 | 2/2003 | Hansen et al. | |
| 6,533,978 B1 | 3/2003 | Wisneski et al. | |
| 6,540,853 B1 | 4/2003 | Suzuki et al. | |
| 6,582,413 B2 | 6/2003 | Krautkramer et al. | |
| 6,582,560 B2 | 6/2003 | Runge et al. | |
| 6,630,096 B2 | 10/2003 | Venturino et al. | |
| 6,645,407 B2 | 11/2003 | Kellenberger et al. | |
| 6,663,611 B2 | 12/2003 | Blaney et al. | |
| 6,706,945 B1 | 3/2004 | Melius et al. | |
| 6,737,491 B2 | 5/2004 | Soerens et al. | |
| 6,767,553 B2 * | 7/2004 | Sun et al. | 424/443 |
| 6,822,135 B2 | 11/2004 | Soerens et al. | |
| 6,887,961 B2 | 5/2005 | Soerens et al. | |
| 6,888,044 B2 | 5/2005 | Fell et al. | |
| 6,964,803 B2 | 11/2005 | Krautkramer et al. | |
| 7,115,321 B2 | 10/2006 | Soerens et al. | |
| 7,754,197 B2 * | 7/2010 | Wu et al. | 424/76.2 |
| 2002/0059993 A1 | 5/2002 | Tanner et al. | |
| 2002/0081930 A1 * | 6/2002 | Jackson et al. | 442/416 |
| 2002/0169428 A1 | 11/2002 | Fell et al. | |
| 2003/0111758 A1 | 6/2003 | Clark et al. | |
| 2003/0111774 A1 | 6/2003 | Kellenberger et al. | |
| 2003/0116888 A1 | 6/2003 | Rymer et al. | |
| 2003/0119394 A1 * | 6/2003 | Ranganathan et al. | 442/79 |
| 2003/0120253 A1 | 6/2003 | Wentzel et al. | |
| 2003/0144637 A1 * | 7/2003 | Sun et al. | 604/359 |
| 2003/0203009 A1 | 10/2003 | MacDonald | |
| 2004/0060112 A1 | 4/2004 | Fell et al. | |
| 2004/0120921 A1 | 6/2004 | Quincy, III et al. | |
| 2004/0122387 A1 | 6/2004 | Long et al. | |
| 2004/0157734 A1 | 8/2004 | Mertens et al. | |
| 2004/0157971 A1 | 8/2004 | Kim | |
| 2004/0175556 A1 | 9/2004 | Clark et al. | |
| 2004/0214499 A1 | 10/2004 | Qin et al. | |
| 2005/0027267 A1 * | 2/2005 | Van Dyke et al. | 604/367 |
| 2005/0080821 A1 | 4/2005 | Ahmed et al. | |
| 2005/0084412 A1 | 4/2005 | MacDonald et al. | |
| 2005/0084438 A1 | 4/2005 | Do et al. | |
| 2005/0084464 A1 | 4/2005 | McGrath et al. | |
| 2005/0084474 A1 | 4/2005 | Wu et al. | |
| 2005/0085144 A1 | 4/2005 | MacDonald et al. | |
| 2005/0113771 A1 * | 5/2005 | MacDonald et al. | 604/359 |
| 2005/0131363 A1 * | 6/2005 | MacDonald et al. | 604/367 |
| 2006/0105963 A1 | 5/2006 | Yang et al. | |
| 2006/0142712 A1 | 6/2006 | Quincy, III | |
| 2006/0173431 A1 | 8/2006 | Laumer et al. | |

FOREIGN PATENT DOCUMENTS

| | | | |
|---|---|---|---|
| EP | 1149594 A1 | 10/2001 | |
| EP | 1149595 A1 | 10/2001 | |
| EP | 1188854 A1 | 3/2002 | |
| EP | 1275404 A1 | 1/2003 | |
| JP | 2006659 | 1/1990 | |
| JP | 9030944 | 2/1997 | |
| WO | WO 9826808 A2 | 6/1998 | |
| WO | WO 9900093 A1 | 1/1999 | |
| WO | WO 9963925 A1 | 12/1999 | |
| WO | WO 9964083 | 12/1999 | |
| WO | WO 0059556 | 10/2000 | |
| WO | WO 0132226 A1 | 5/2001 | |
| WO | WO 02095112 A1 | 11/2002 | |
| WO | WO 03020193 | 3/2003 | |

OTHER PUBLICATIONS

English Abstract for JP 9030944, Feb. 4, 1997.
English Abstract for DE 10017446, Nov. 8, 2001.
Article—*Adsorption of Gases in Multimolecular Layers*, Brunauer et al., The Journal of the American Chemical Society, vol. 60, Jan.-Jun. 1938, pp. 309-319.
Article—*Analysis of Malodorous Volatile Substances of Human Waste: Feces and Urine*, Sato et al., Journal of Health Science, vol. 47, 2001, pp. 483-490.
International Search Report dated Jan. 22, 2007, for International Application No. PCT/US2006/032210 filed Aug. 17, 2006.
Related U.S. Patent Application Form.
Fish et al., U.S. Appl. No. 10/687,425, filed Oct. 16, 2003, Odor Absorbing Extrudates.

* cited by examiner

FIG. 1

FIG. 2 ized a fibrous sheet to form a plurality of individual fibers;
ABSORBENT ARTICLES WITH IMPROVED ODOR CONTROL

RELATED APPLICATIONS

The present application is a divisional application of U.S. application Ser. No. 11/263,598, filed on Oct. 31, 2005, which is incorporated herein in its entirety by reference thereto for all purposes.

BACKGROUND OF THE INVENTION

Odor control agents have been incorporated into absorbent articles for a variety of reasons. For instance, U.S. Patent Application Publication No. 2003/0203009 to MacDonald describes an odor control agent that is formed from high surface area particles modified with a metal ion. Although such modified particles are effective in reducing odor, problems may nevertheless arise when attempting to incorporate the odor control agents into an absorbent article. For example, it is often difficult to retain loose particles in the desired location for efficacious adsorption of odors from urine or other bodily fluids. Additionally, separate addition of odor control agents into absorbent articles requires investment for capital equipment and results in increased process complexity.

As such, a need currently exists for an improved technique for incorporating an odor control agent into an absorbent article.

SUMMARY OF THE INVENTION

In accordance with one embodiment of the present invention, an absorbent article having odor control properties is disclosed. The article comprises an absorbent core that includes an airformed web, the airformed web containing a matrix of fluff pulp fibers in which is homogeneously distributed odor control particles.

In accordance with another embodiment of the present invention, a method for forming an absorbent web with odor control properties is disclosed. The method comprises treating a fibrous sheet with a coating formulation that comprises odor control particles; fiberizing the sheet to form a plurality of individual fibers; entraining the fibers in a gaseous stream; and thereafter, depositing the fibers onto a forming surface.

In accordance with still another embodiment of the present invention, a method for forming an absorbent web with odor control properties is disclosed. The method comprises treating a superabsorbent material with a coating formulation, the coating formulation comprising odor control particles; fiberizing a fibrous sheet to form a plurality of individual fibers; entraining the fibers in a gaseous stream; intermixing the treated superabsorbent material with the entrained fibers; and thereafter, depositing the fibers and the treated superabsorbent material onto a forming surface.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a technique for incorporating odor control particles into an absorbent article. More specifically, the odor control particles are "homogenously" distributed (e.g., distributed in a substantially uniform manner) within an airformed fiber matrix of an absorbent core of an absorbent article. An absorbent core containing such a homogeneously distributed odor control particles may possess a greater surface area for contacting malodorous compounds, thereby increasing the likelihood of odor reduction.

1. Odor Control Particles

Any of a variety of odor control particles may be used in accordance with the present invention that are capable of imparting odor control to an absorbent article. For example, inorganic oxide particles, such as silica, alumina, zirconia, magnesium oxide, titanium dioxide, iron oxide, zinc oxide, copper oxide, zeolites, clays (e.g., smectite clay), combinations thereof, and so forth, may be employed in some embodiments of the present invention. Various examples of such inorganic oxide particles are described in U.S. Patent Application Publication Nos. 2003/0203009 to MacDonald; 2005/0084412 to Macdonald, et al.; 2005/0085144 to Macdonald, et al.; 2005/0084464 to McGrath, et al.; 2005/0084474 to Wu, et al.; and 2005/0084438 to Do, et al., which are incorporated herein in their entirety by reference thereto for all purposes.

The inorganic oxide particles may possess various forms, shapes, and sizes depending upon the desired result. For instance, the particles may be in the shape of a sphere, crystal, rod, disk, tube, string, etc. If desired, the particles may be relatively nonporous or solid. That is, the particles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. The average size of the particles is generally less than about 500 microns, in some embodiments less than about 100 microns, in some embodiments less than about 100 nanometers, in some embodiments from about 1 to about 50 nanometers, in some embodiments from about 2 to about 50 nanometers, and in some embodiments, from about 4 to about 20 nanometers. As used herein, the average size of a particle refers to its average length, width, height, and/or diameter. Further, the particles may also have a high surface area, such as from about 50 square meters per gram ($m^2/g$) to about 1000 $m^2/g$, in some embodiments from about 100 $m^2/g$ to about 600 $m^2/g$, and in some embodiments, from about 180 $m^2/g$ to about 240 m²/g. Surface area may be determined by the physical gas adsorption (B.E.T.) method of Bruanauer, Emmet, and Teller, Journal of American Chemical Society, Vol. 60, 1938, p. 309, with nitrogen as the adsorption gas. Without intending to be limited by theory, it is believed that particles having such a small size and high surface area may improve the adsorption capability for many malodorous compounds. Moreover, it is believed that the solid nature, i.e., low pore volume, of the particles may enhance the uniformity and stability of the particles, without sacrificing their odor adsorption characteristics.

The "zeta potential" of the particles may also vary as desired. For example, the particles may possess a negative zeta potential, such as less than about 0 millivolts (mV), in some embodiments less than about −10 mV, and in some embodiments, less than about −20 mV. Commercially available examples of particles having a negative zeta potential include Snowtex-C, Snowtex-O, Snowtex-PS, and Snowtex-OXS, which are silica nanoparticles available from Nissan Chemical of Houston, Tex. Alternatively, the particles may have a zeta potential of greater than about +20 millivolts (mV), in some embodiments greater than about +30 mV, and in some embodiments, greater than about +40 mV. By possessing a positive surface charge, the particles are well suited for being affixed to fibers that carry a negative surface charge (e.g., cellulosic fibers) through ionic attraction. Depending upon the difference in charge between the particles and the surface of the fibers (including van der Waals forces), the bond in some applications may be relatively permanent and substantive. Consequently, the particles may be affixed to fibers without the use of chemical binders or other attachment structures.

A positive zeta potential may be imparted to the particles of the present invention in a variety of different ways. In one embodiment, the particles are formed entirely from a positively charged material. For example, alumina particles may be used for odor reduction in accordance with the present invention. Some suitable alumina particles are described in U.S. Pat. No. 5,407,600 to Ando, et al., which is incorporated herein in its entirety by reference thereto for all purposes. Further, examples of commercially available alumina particles include, for instance, Aluminasol 100, Aluminasol 200, and Aluminasol 520, which are available from Nissan Chemical Industries Ltd. Alternatively, the positive zeta potential may be imparted by a continuous or discontinuous coating present on the surface of a core material. In some instances, these particles may actually possess a better stability over various pH ranges than particles formed entirely from positively charged materials. In one particular embodiment, for example, the particles are formed from silica particles coated with alumina. A commercially available example of such alumina-coated silica particles is Snowtex-AK, which is available from Nissan Chemical of Houston, Tex.

The inorganic oxide particles may also be modified with one or more transition metals to improve their odor control properties. More specifically, without being limited by theory, it is believed that the transition metal provides one or more active sites for capturing and/or neutralizing a malodorous compound. The active sites may be free, or may be weakly bound by water molecules or other ligands so that they are replaced by a malodorous molecule when contacted therewith. In addition, the particles still have the large surface area that is useful in adsorbing other malodorous compounds. Examples of some suitable transition metals that may be used in the present invention include, but are not limited to, scandium, titanium, vanadium, chromium, manganese, iron, cobalt, nickel, copper, zinc, silver, gold, and so forth. Single metallic, as well as dinuclear, trinuclear, and cluster systems may be used.

The transition metal may be applied to the particles in a variety of ways. For instance, particles may simply be mixed with a solution containing the appropriate transition metal in the form of a salt, such as those containing a copper ion ($Cu^{+2}$), silver ion ($Ag^+$), gold ion ($Au^+$ and $Au^{+3}$), iron (II) ion ($Fe^{+2}$), iron (III) ion ($Fe^{+3}$), and so forth. Such solutions are generally made by dissolving a metallic compound in a solvent resulting in free metal ions in the solution. Generally, the metal ions are drawn to and adsorbed onto the particles due to their electric potential differences, i.e., they form an "ionic" bond. In many instances, however, it is desired to further increase the strength of the bond formed between the metal and particles, e.g., to form a coordinate and/or covalent bond. Although ionic bonding may still occur, the presence of coordinate or covalent bonding may have a variety of benefits, such as reducing the likelihood that any of the metal will remain free during use (e.g., after washing). Further, a strong adherence of the metal to the particles also optimizes odor adsorption effectiveness.

If desired, more than one type of transition metal may be bound to a particle. This has an advantage in that certain metals may be better at removing specific malodorous compounds than other metals. Likewise, different types of modified particles may be used in combination for effective removal of various malodorous compounds. In one embodiment, for instance, copper-modified silica particles are used in combination with manganese-modified silica particles. By using two different modified particles in combination, numerous malodorous compounds may be more effectively removed. For example, the copper-modified particle may be more effective in removing sulfur and amine odors, while the manganese-modified particle may be more effective in removing carboxylic acids. The ratio of the transition metal to the particles may be selectively varied to achieve the desired results. In most embodiments, for example, the mole ratio of the transition metal to the particles is at least about 10:1, in some embodiments at least about 50:1, and in some embodiments, at least about 100:1.

In addition to inorganic oxide particles, other particulate odor control agents may be employed in the present invention. For example, a quinone powder having odor control characteristics may also be used in the present invention. Quinone powders may be prepared by drying a quinone compound in an oven and then converting the dried material to a powder using a milling device, such as a ball mill, bead mill, vibratory mill, sand mill, colloid mill, etc. Suitable dispersing agents may be, for example, condensation products of naphthalene sulfonic acid and formaldehyde, lignosulfonates or nonionic and anionic surface-active compounds. The resulting powder generally has an average particle size of from about 0.01 microns to about 20 microns, in some embodiments from about 0.5 microns to about 10 microns, and in some embodiments, from about 0.03 microns to about 6 microns. As used herein, the average size of a particle refers to its average length, width, height, and/or diameter. Some suitable anthraquinone powders are commercially available from Noveon Hilton Davis, Inc. of Cincinnati, Ohio and Sigma-Aldrich Chemical Co., Inc. of St. Louis, Mo.

Generally speaking, quinones refer to a class of compounds that possess a quinoid ring, such as anthraquinones, naphthaquinones, benzoquinones, hydroquinones, and so forth. Anthraquinones, for instance, have the following general formula:

The numbers 1-8 shown in the general formula represent a location on the fused ring structure at which substitution of a functional group may occur. Some examples of such functional groups that may be substituted on the fused ring structure include halogen groups (e.g., chlorine or bromine groups), sulfonyl groups (e.g., sulfonic acid salts), alkyl groups, benzyl groups, amino groups (e.g., primary, secondary, tertiary, or quaternary amines), carboxy groups, cyano groups, hydroxy groups, phosphorous groups, etc. Functional groups that result in an ionizing capability are often referred to as "chromophores." Substitution of the ring structure with a chromophore causes a shift in the absorbance wavelength of the compound. Thus, depending on the type of chromophore (e.g., hydroxyl, carboxyl, amino, etc.) and the extent of substitution, a wide variety of quinones may be formed with varying colors and intensities. Other functional groups, such as sulfonic acids, may also be used to render certain types of compounds (e.g., higher molecular weight anthraquinones) water-soluble.

Anthraquinone compounds may be classified for identification by their Color Index (CI) number, which is sometimes called a "standard." For instance, some suitable anthraquinones that may be used in the present invention, as classified by their "CI" number, include Acid Black 48, Acid Blue 25 (D&C Green No. 5), Acid Blue 40, Acid Blue 41, Acid Blue 45, Acid Blue 80, Acid Blue 129, Acid Green 25, Acid Green 27, Acid Green 41, Acid Violet 43, Mordant Red 11 (Alizarin), Mordant Black 13 (Alizarin Blue Black B), Mordant Red 3 (Alizarin Red S), Mordant Violet 5 (Alizarin Violet 3R), Alizarin Complexone, Natural Red 4 (Carminic Acid), Disperse Blue 1, Disperse Blue 3, Disperse Blue 14, Natural Red 16 (Purpurin), Natural Red 8, Reactive Blue 2 (Procion Blue HB), Reactive Blue 19 (Remazol Brilliant Blue R); and so forth. The structures of Acid Blue 25, Acid Green 41, Acid Blue 45, Mordant Violet 5, Acid Blue 129, Acid Green 25, and Acid Green 27 are set forth below:

Acid Blue 25

Acid Green 41

Acid Blue 45

Mordant Violet 5

Acid Blue 129

Acid Green 25

Acid Green 27

As stated above, other quinones may also be used in the present invention. For example, naphthaquinones may be used that have the following general formula:

The locations 1-6 of the naphthaquinone compounds may be substituted with functional groups in the manner described above. For instance, suitable examples of naphthaquinone compounds that may be used in the present invention include 1,4 naphthaquinone and 1,2 naphthaquinone, which have the following structures:

1,4-Naphthaquinone      1,2-Naphthaquinone

Without intending to be limited by theory, it is believed that the odor caused by many compounds is eliminated by the transfer of electrons to and/or from the malodorous compound. Specifically, oxidation of malodorous compounds via a reduction/oxidation ("redox") reaction is believed to inhibit the production of the characteristic odor associated therewith. The discovery that certain quinone compounds are able to eliminate odor is believed to be due to their ability to function as an oxidizing agent in a redox reaction. Many common malodorous compounds (e.g., ethyl mercaptan) are capable of being oxidized (i.e., donate electrons) via a redox reaction. Upon oxidation, the odors associated with such compounds are often eliminated or at least lessened. It is also believed that the reduction of the quinone compound via the redox reaction is readily reversible, and thus the reduced quinone compound may be oxidized by any known oxidizing agent (e.g., oxygen, air, etc.). The reduction/oxidation reactions are rapid and may take place at room temperature. Thus, although the odor control mechanism may consume the quinone compounds, they may simply be regenerated by exposure to air. Thus, long-term odor control may be achieved without significantly affecting the ability of the quinone compound to impart the desired color.

In addition to their ability to oxidize malodorous compounds, the chemical structure of certain quinone compounds may help improve odor elimination. For example, anthraquinone compounds that have at least one unsubstituted ring may result in better odor inhibition than those that are substituted at each ring with a functional group. Interestingly, anthraquinone compounds that are unsubstituted at the "first" ring (i.e., positions 5 through 8) appear to be particularly effective in reducing odor. Suitable examples of anthraquinone compounds that are unsubstituted at locations at their first ring include, but are not limited to, Acid Blue 25, Acid Blue 129, Acid Green 25, and Acid Green 27, the structures of which are set forth above. Other exemplary odor control quinone compounds are described in U.S. Patent Application Publication No. 2005/0131363 to Macdonald, et al., which is incorporated herein in its entirety by reference thereto for all purposes.

In the embodiments described above, the odor control agent inherently possesses a particulate form to increase the surface area available for contact with malodorous compounds and to facilitate fiber application. In some cases, however, the odor control particles may be formed by pre-treating carrier particles with an odor control agent. For example, carrier particles may be treated with quinone compounds, such as described above. Although not required, the carrier particles may also have odor control properties. In one embodiment, for instance, the carrier particles may be inorganic oxide particles. Superabsorbent particles may also serve as useful carrier particles. Superabsorbent particles are water-swellable materials capable of absorbing at least about 20 times its weight and, in some cases, at least about 30 times its weight in an aqueous solution containing 0.9 weight percent sodium chloride. The superabsorbent particles may be natural, synthetic and modified natural polymers and materials. Examples of synthetic superabsorbent material polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful in the present invention. Particularly suitable superabsorbent polymers are HYSORB 8800AD (BASF of Charlotte, N.C. and FAVOR SXM 9300 (available from Degussa Superabsorber of Greensboro, N.C.).

Regardless of the particular odor control particles employed, they may be dispersed in a solvent to form a coating formulation that is then applied to the fibers. Any solvent capable of dispersing or dissolving the components is suitable, such as water; alcohols, such as ethanol or methanol; dimethylformamide; dimethyl sulfoxide; hydrocarbons, such as pentane, butane, heptane, hexane, toluene and xylene; ethers such as diethyl ether and tetrahydrofuran; ketones and aldehydes, such as acetone and methyl ethyl ketone; acids, such as acetic acid and formic acid; and halogenated solvents, such as dichloromethane and carbon tetrachloride; as well as mixtures thereof. The concentration of solvent in the coating formulation is generally high enough to allow an economically feasible application process. If the amount of solvent is too large, however, the amount of odor control particles might be too low to provide the desired odor reduction. Although the actual concentration of solvent employed will generally depend on the type of odor control particles and the fibers to which they are applied, they are nonetheless typically present in an amount from about 40 wt. % to about 99 wt. %, in some embodiments from about 65 to about 98 wt. %, and in some embodiments, from about 80 wt. % to about 96 wt. % of the coating formulation. The amount of the odor control particles added to the coating formulation will vary depending on the amount of odor reduction desired and the maximum concentration that may be dispersed or dissolved in the coating solution. For example, the odor control particles may constitute from about 0.01 wt. % to about 20 wt. %, in some embodiments from about 0.1 wt. % to about 15 wt. %, and in some embodiments, from about 0.5 wt. % to about 10 wt. % of the coating formulation. The solids content of the coating formulation may also be varied to achieve the extent of odor reduction desired. For example, the coating formulation may have a solids content of from about 1% to about 60%, in some embodiments from about 2% to about 35%, and in some embodiments, from about 4% to about 20%. By varying the solids content of the formulation, the presence of the odor control particles may be controlled. For example, to form a coating formulation with a higher level of odor control particles, the formulation may be provided with a relatively high solids content so that a greater percentage of the particles are incorporated into the formulation during the application process.

II. Fiber Treatment

As noted above, the odor control particles of the present invention may be homogeneously distributed within a matrix of fibers, such as hydrophilic fibers, used to form the absorbent core of an absorbent article. Hydrophilic fibers may include natural and/or synthetic fluff pulp fibers. The fluff pulp fibers may be kraft pulp, sulfite pulp, thermomechanical pulp, etc. In addition, the fluff pulp fibers may include high-average fiber length pulp, low-average fiber length pulp, or mixtures of the same. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas-fir, true firs, pine (e.g., southern pines), spruce (e.g., black spruce), combinations thereof, and so forth. Northern softwood kraft pulp fibers may be used in the present invention. One example of commercially available southern softwood kraft pulp fibers suitable for use in the present invention include those available from Weyerhaeuser Company with offices in Federal Way, Wash. under the trade designation of "NB-416." Another suitable fluff pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. Eucalyptus kraft pulp fibers may be particularly desired to increase softness, enhance brightness, increase opacity, and change the pore structure of the sheet to increase its wicking ability.

In addition, synthetic fibers may also be utilized. Some suitable polymers that may be used to form the synthetic fibers include, but are not limited to: polyolefins, such as, polyethylene, polypropylene, polybutylene, and so forth; polyesters, such as polyethylene terephthalate, poly(glycolic acid) (PGA), poly(lactic acid) (PLA), poly($\beta$-malic acid) (PMLA), poly($\epsilon$-caprolactone) (PCL), poly($\rho$-dioxanone) (PDS), poly(3-hydroxybutyrate) (PHB), and so forth; and, polyamides, such as nylon and so forth. Synthetic or natural cellulosic polymers, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. Non-wood fibers may also be used, including fiber originating from hemp, straw, flax, bagasse, and mixtures thereof may be used in the present invention.

To homogeneously distribute the odor control particles within the matrix of fibers, any of a variety of application techniques may be employed. For example, the odor control particles may be topically applied to a dry lap sheet of fluff pulp. The dry lap sheet may then be subjected to a fiberizing process that breaks the sheet into a plurality of individual fibers. These individual fibers may then be supplied to a forming chamber that deposits the fibers onto a foraminous surface to form an airformed web. Due to the vigorous mixing imparted by the fiberizing process, the odor control particles thus become homogeneously distributed throughout the web structure. Additionally, a superabsorbent material that is pre-coated with an odor control agent may be separately injected into the forming chamber where it will mix with the fibers.

Various specific embodiments of the aforementioned techniques will now be described in greater detail. It should be understood, however, that the embodiments described are merely exemplary, and that various other embodiments are also contemplated by the present invention. In this regard, referring to FIG. 1, one embodiment of a forming apparatus 20 that may be used in the present invention is depicted. As shown, the apparatus 20 includes a fiberizer 44, such as a rotary hammermill, rotatable picker roll, or any other conventional fiberizing device. A dry lap sheet 80 of fluff pulp is supplied to the fiberizer 44 to form a plurality of individual fibers. In one embodiment of the present invention, the dry lap sheet is pre-treated with odor control particles using conventional techniques, such as printing, dipping, spraying, melt extruding, solvent coating, powder coating, and so forth. The percent coverage and add-on level of the odor control particles may be selectively varied to achieve any desired distribution within the final web. For instance, the percent coverage of the odor control particles may be greater than about 50%, in some embodiments greater than about 80%, and in some embodiments, approximately 100% of the area of a given surface. Likewise, the odor control particles are typically applied in an amount from about 0.01 wt. % to about 20 wt. %, in some embodiments from about 0.1 wt. % to about 10 wt. %, and in some embodiments, from about 1 wt. % to about 5 wt. % based on the weight of pulp fibers.

Figure 1:
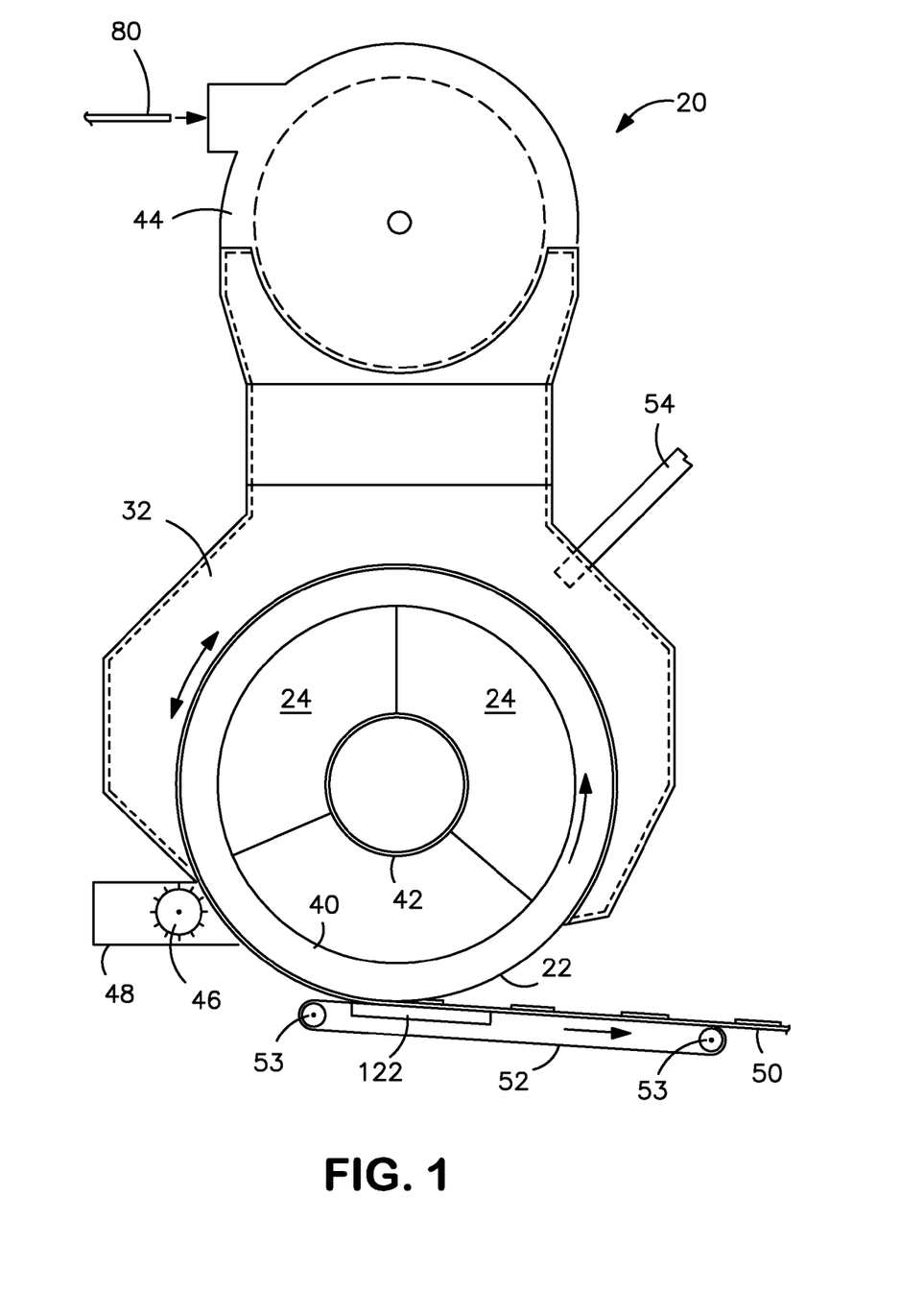
FIG. 1 is a schematic view of one embodiment of a forming apparatus that may be used in the present invention.

Once fiberized, the individual fibers are entrained in a stream of a gaseous medium (e.g., air), and then ejected or otherwise introduced into a forming chamber 32. Although illustrated below the fiberizer 44, the forming chamber 32 may also be positioned at any other location, such as to the side or at a remote location that is spaced away from the fiberizer 44. The forming chamber 32 may direct and concentrate the gas-entrained fibers and provide a desired velocity profile in the stream. Various suitable forming chamber configurations are described, for instance, in U.S. Pat. Nos.

4,927,582 to Bryson and 6,630,096 to Venturino, et al., which are incorporated herein in their entirety by reference thereto for all purposes.

The apparatus 20 also includes a movable, foraminous forming surface 22 onto which a fibrous web 50 is formed. Typically, the forming surface 22 is provided by a foraminous, air permeable material, such as a wire forming cloth, screen, perforated plate, fabric, belt, drum, etc. Suitable forming belts are commercially available from the Paper Converting Machine Co. of Green Bay, Wis. and from Curt G. Joa, Inc. of Sheboygan Falls, Wis. In the illustrated embodiment, the forming surface 22 is provided by a forming drum 40. During use, the forming drum 40 is rotated in a desired direction by a drum drive shaft (not shown) that is operatively joined to a drive mechanism (not shown). The drive mechanism may include an electric or other motor that is directly or indirectly coupled to the drive shaft. If desired, the forming surface 22 may include a series of separately removable, forming sections that are distributed circumferentially along the periphery of the forming drum 40. Such forming sections may optionally provide a selected repeat pattern that is formed in the resulting fibrous web. The repeat pattern may correspond to a desired shape of an individual absorbent pad that is intended for assembly or other placement in an absorbent article. Suitable forming drum systems are described in more detail in U.S. Pat. Nos. 4,666,647 to Enloe, et al.; 4,761,258 to Enloe; and 6,330,735 to Hahn, et al., which are incorporated herein in their entirety by reference thereto for all purposes.

The interior space of the forming drum 40 may include a vacuum zone having the general form of an arcuate segment located at the portion of the forming surface 22 positioned within the forming chamber 32. In the illustrated embodiment, for instance, the vacuum zone is located adjacent to the forming chamber 32 and may include features provided by a vacuum duct 24. The portion of the forming drum 40 positioned within the boundaries of the forming chamber 32 may delimit or otherwise provide a lay-down zone of the forming surface 22. Such a vacuum lay-down zone may, for example, constitute a circumferential, cylindrical surface portion of the rotatable drum 40. A pressure differential is imposed on the surface of the vacuum lay-down zone by a conventional vacuum source (e.g., vacuum pump, an exhaust blower, etc.) to provide a relatively low pressure under the forming surface 22. Under the influence of the vacuum source, a conveying gas stream is thus drawn through the forming surface 22 into the interior of the forming drum 40, and subsequently passed out of the drum through a vacuum supply conduit 42. As the gas-entrained fibers impinge on the foraminous forming surface 22, a gas (e.g., air) is passed through the forming surface 22 to cause the fibers to be retained on the surface to form a fibrous web 50.

If desired, drum rotation may then pass the fibrous web 50 to a scarfing zone where excess thickness may be trimmed and removed to a predetermined extent. More specifically, the scarfing system may include a scarfing chamber 48 and a scarfing roll 46 positioned therein. The scarfing roll 46 rotates in a direction opposite to the movement direction of the laid fibrous web 50. Alternatively, the scarfing roll 46 may be rotated to provide a co-directional movement of the roller surface relative to the surface of the forming drum proximate thereto. In either case, the rotational speed of the scarfing roll 46 is selected to provide an effective scarfing action against the contacted surface of the formed fibrous web 50 to abrade excess fibrous material therefrom. If desired, the removed fibrous material may be recycled back into the forming chamber 32 or the fiberizer 44, as desired. Additionally, the scarfing roll 46 may rearrange and redistribute the web material along the longitudinal machine-direction of the web and/or along the lateral cross-direction of the web.

After the scarfing operation, the portion of the forming surface 22 that is carrying the fibrous web 50 may be moved to an optional pressure blow-off zone of the forming drum system. In the blow-off zone, a gas (e.g., air) may be introduced under pressure and directed radially outwardly against the fibrous web on the portion of the forming surface that becomes aligned with the blow-off zone. The gas pressure may cause the fibrous web to release from the forming surface 22 onto a suitable web transport mechanism. The web transporter may receive the fibrous web 50 from the forming drum 40 and convey it for further processing. Suitable web transporters may include conveyer belts, vacuum drums, transport rollers, electromagnetic suspension conveyors, fluid suspension conveyors or the like, as well as combinations thereof. As shown, for instance, the web transporter may include a conveyor belt 52 disposed about rollers 53. In a particular embodiment, a vacuum suction box 122 is located below the conveyor belt 52 to help remove the web 50 from the forming surface 22. The vacuum box 122 opens onto the belt 52 and draws gas through perforations in the conveyor belt 52. In turn, this flow of gas draws the web 50 away from the forming surface 22. The vacuum box 122 may be employed with or without the use of a positive pressure in the blow-off zone. The removed fibrous web 50 may provide an interconnected series of pads, and each pad may have a selected surface contour that substantially matches the contour provided by the various, corresponding portions of the forming surface 22 upon which each individual pad was formed.

It will be readily apparent that various conventional devices and techniques may be employed to further process the web 50. For example, various conventional devices and techniques may be employed to sever fibrous web 50 into predetermined lengths to provide selected laid fibrous articles. The severing system may, for example, include a die cutter, a water cutter, a rotary knives, reciprocating knives, energy beam cutters, particle beam cutters or the like, as well as combinations thereof. After severing, the discrete fibrous pads 50 may be transported and delivered for further processing operations.

In addition to or on in conjunction with being pre-treated onto a dry lap sheet, the odor control particles may also be applied substantially concurrently with the formation of the web. For example, odor control particles may be pre-coated onto a superabsorbent material and then introduced into the forming chamber 32. The amount of odor control particles applied to the superabsorbent material may generally vary to achieve the desired effect. For example, the odor control particles may be applied in an amount from about 0.01% to about 20% by weight, in some embodiments from about 0.1% to about 10% by weight, and in some embodiments, from about 0.5% to about 5% by weight of the superabsorbent material. Thereafter, the treated superabsorbent material may then be delivered into the forming chamber 32. Upon intermixing with the fibers, the odor control particles may thus become homogeneously distributed within the resulting fibrous web 50. Additionally, both fibers and superabsorbents treated with odor control particles could be placed in a fibrous web. In such cases, the odor control particles may be the same or different.

The superabsorbent material (optionally pre-coated with the odor control particles) may be introduced into the forming chamber 32 using conventional mechanisms, such as pipes, channels, spreaders, nozzles and so forth, as well as combinations thereof. In the illustrated embodiment, for example, the apparatus 20 may include a nozzle 54 that dispenses the odor control particles into the forming chamber 32. The nozzle 54 may be any conventional component of a spraying system, such as a hydraulic spray system, air atomizing spray system, ultra-sonic spray system and so forth. In desired arrangements, a flat-pattern spray nozzle may be used in which the longest dimension of the spray pattern is aligned generally along the cross-direction of the apparatus. A suitable flat-pattern spray nozzle is a UNIJET® spray nozzle available from the Spraying Systems Co. of Wheaton Ill. In particular arrangements, the spray nozzle may have a spray orifice diameter that is within the range of about 0.25 to 2.5 millimeters.

The spray nozzle 54 may be placed a certain distance above the forming surface 22, with the distance being measured along a straight reference line that intersects the center of the outlet orifice of the nozzle 54 and extends perpendicular to the forming surface 22 at the local position of the spray nozzle 54. The distance may be selectively varied to achieve the desired results. If the distance is too small, the spraying process may excessively interfere with the formation of the absorbent web and increase the likelihood of plugging in the nozzle. On the other hand, if the distance is too large, it may be difficult to maintain the desired distribution stream of the odor control particles from the nozzle. Thus, the distance is typically from about 10 millimeters to about 250 millimeters, in some embodiments from about 40 millimeters to about 200 millimeters, and in some embodiments, from about 80 millimeters to about 150 millimeters.

When applied to fluff pulp, the odor control particles typically constitute from about 0.01 wt. % to about 25 wt. %, in some embodiments from about 0.1 wt. % to about 15 wt. %, and in some embodiments, from about 0.5 wt. % to about 10 wt. % of the treated fluff pulp fibers. The treated fluff pulp fibers may also be blended with untreated fluff pulp fibers or other fibers, polymers, or superabsorbent material to form the fibrous web. In such cases, the percentage of treated pulp fibers may range from about 5 wt. % to about 100 wt. %, in some embodiments from about 10 wt. % to about 100 wt. %, and in some embodiments from about 10 wt. % to about 90 wt. % of the fibrous web. The total amount of odor control particles in the fibrous web may likewise range from about 0.01 wt. % to about 20 wt. %, in some embodiments from about 0.1 wt. % to about 10 wt. %, and in some embodiments, from about 0.5 wt. % to about 5 wt. % of the web. Superabsorbent content may range from 0% up to about 90% of the fibrous web.

III. Absorbent Articles

When formed in accordance with the present invention, the resulting fibrous web contains odor control particles that are capable of reducing or inhibiting one or more odors. In addition, due to their homogeneous distribution within the web, the odor control particles are better able to contact malodorous compounds over the entire surface of the web. Such an odor-reducing Web may be used in a wide variety of applications. In one particular embodiment, for example, the fibrous web may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth.

Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core. The treated fibrous web of the present invention may be employed as any one or more of the liquid transmissive (non-retentive) and absorbent layers, and is desirably used to form the absorbent core. For example, the treated fibrous web may form the entire absorbent core. Alternatively, the treated fibrous web may form only a portion of the core, such as a layer of an absorbent composite that includes one or more additional layers (e.g., wet-formed paper webs, coform webs, etc.). Regardless, the odor control particles contained within the fibrous web may contact malodorous compounds absorbed by the absorbent core (e.g., urine) and thereby reduce the amount of odor released by the article.

Figure 2:
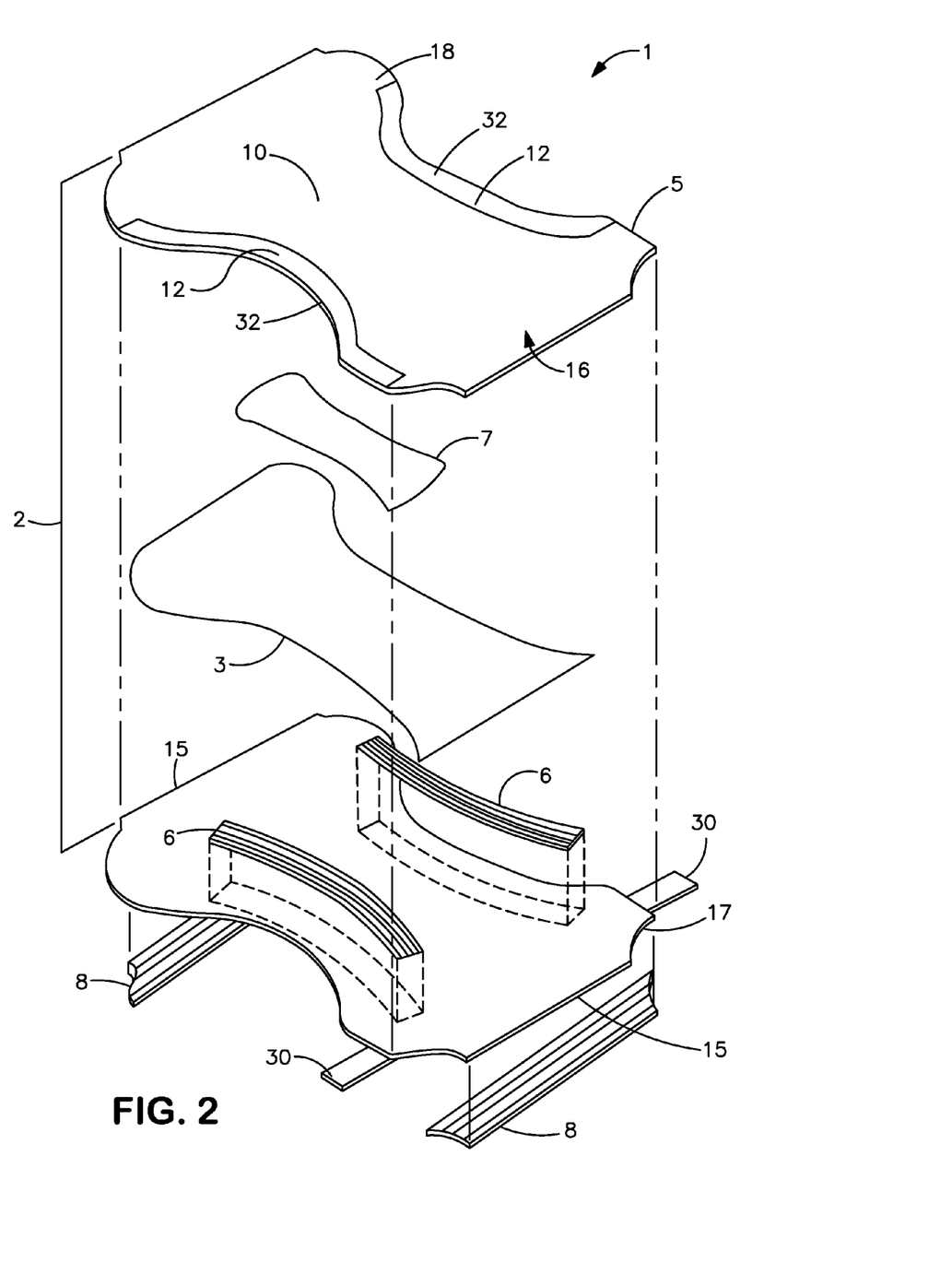
FIG. 2 illustrates a perspective view of an absorbent article that may be formed according to one embodiment of the present invention.

Various embodiments of an absorbent article that may be formed according to the present invention will now be described in more detail. For purposes of illustration only, an absorbent article is shown in FIG. 2 as a diaper 1. However, as noted above, the invention may be embodied in other types of absorbent articles, such as incontinence articles, sanitary napkins, diaper pants, feminine napkins, children's training pants, and so forth. In the illustrated embodiment, the diaper 1 is shown as having an hourglass shape in an unfastened configuration. However, other shapes may of course be utilized, such as a generally rectangular shape, T-shape, or I-shape. As shown, the diaper 1 includes a chassis 2 formed by various components, including an outer cover 17, bodyside liner 5, absorbent core 3, and surge layer 7. It should be understood, however, that other layers may also be used in the present invention. Likewise, one or more of the layers referred to in FIG. 2 may also be eliminated in certain embodiments of the present invention.

The outer cover 17 is typically formed from a material that is substantially impermeable to liquids. For example, the outer cover 17 may be formed from a thin plastic film or other flexible liquid-impermeable material. In one embodiment, the outer cover 17 is formed from a polyethylene film having a thickness of from about 0.01 millimeter to about 0.05 millimeter. If a more cloth-like feeling is desired, the outer cover 17 may be formed from a polyolefin film laminated to a nonwoven web. For example, a stretch-thinned polypropylene film having a thickness of about 0.015 millimeter may be thermally laminated to a spunbond web of polypropylene fibers. The polypropylene fibers may have a denier per filament of about 1.5 to 2.5, and the nonwoven web may have a basis weight of about 17 grams per square meter. The outer cover 17 may also include bicomponent fibers, such as polyethylene/polypropylene bicomponent fibers. In addition, the outer cover 17 may also contain a material that is impermeable to liquids, but permeable to gases and water vapor (i.e., "breathable"). This permits vapors to escape from the absorbent core 3, but still prevents liquid exudates from passing through the outer cover 17.

The diaper 1 also includes a bodyside liner 5. The bodyside liner 5 is generally employed to help isolate the wearer's skin from liquids held in the absorbent core 3. For example, the liner 5 presents a bodyfacing surface that is typically compliant, soft feeling, and non-irritating to the wearer's skin. Typically, the liner 5 is also less hydrophilic than the absorbent core 3 so that its surface remains relatively dry to the wearer. The liner 5 may be liquid-permeable to permit liquid to readily penetrate through its thickness. The bodyside liner 5 may be formed from a wide variety of materials, such as porous foams, reticulated foams, apertured plastic films, natural fibers (e.g., wood or cotton fibers), synthetic fibers (e.g., polyester or polypropylene fibers), or a combination thereof. In some embodiments, woven and/or nonwoven fabrics are used for the liner 5. For example, the bodyside liner 5 may be formed from a meltblown or spunbonded web of polyolefin fibers. The liner 5 may also be a bonded-carded web of natural and/or synthetic fibers. The liner 5 may further be composed of a substantially hydrophobic material that is optionally treated with a surfactant or otherwise processed to impart a desired level of wettability and hydrophilicity. The surfactant may be applied by any conventional method, such as spraying, printing, brush coating, foaming, and so forth. When utilized, the surfactant may be applied to the entire liner 5 or may be selectively applied to particular sections of the liner 5, such as to the medial section along the longitudinal centerline of the diaper. The liner 5 may further include a composition that is configured to transfer to the wearer's skin for improving skin health. Suitable compositions for use on the liner 5 are described in U.S. Pat. No. 6,149,934 to Krzvsik et al., which is incorporated herein in its entirety by reference thereto for all purposes.

As illustrated in FIG. 2, the diaper 1 may also include a surge layer 7 that helps to decelerate and diffuse surges or gushes of liquid that may be rapidly introduced into the absorbent core 3. Desirably, the surge layer 7 rapidly accepts and temporarily holds the liquid prior to releasing it into the storage or retention portions of the absorbent core 3. In the illustrated embodiment, for example, the surge layer 7 is interposed between an inwardly facing surface 16 of the bodyside liner 5 and the absorbent core 3. Alternatively, the surge layer 7 may be located on an outwardly facing surface 18 of the bodyside liner 5. The surge layer 7 is typically constructed from highly liquid-permeable materials. Suitable materials may include porous woven materials, porous nonwoven materials, and apertured films. Some examples include, without limitation, flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. Other examples of suitable surge layers 7 are described in U.S. Pat. No. 5,486,166 to Ellis, et al. and U.S. Pat. No. 5,490,846 to Ellis, et al., which are incorporated herein in their entirety by reference thereto for all purposes.

Besides the above-mentioned components, the diaper 1 may also contain various other components as is known in the art. For example, the diaper 1 may also contain a substantially hydrophilic tissue wrapsheet (not illustrated) that helps maintain the integrity of the fibrous structure of the absorbent core 3. The tissue wrapsheet is typically placed about the absorbent core 3 over at least the two major facing surfaces thereof, and composed of an absorbent cellulosic material, such as creped wadding or a high wet-strength tissue. The tissue wrapsheet may be configured to provide a wicking layer that helps to rapidly distribute liquid over the mass of absorbent fibers of the absorbent core 3. The wrapsheet material on one side of the absorbent fibrous mass may be bonded to the wrapsheet located on the opposite side of the fibrous mass to effectively entrap the absorbent core 3.

Furthermore, the diaper 1 may also include a ventilation layer (not shown) that is positioned between the absorbent core 3 and the outer cover 17. When utilized, the ventilation layer may help insulate the outer cover 17 from the absorbent core 3, thereby reducing dampness in the outer cover 17. Examples of such ventilation layers may include breathable laminates (e.g., nonwoven web laminated to a breathable film), such as described in U.S. Pat. No. 6,663,611 to Blaney, et al., which is incorporated herein in its entirety by reference thereto for all purpose.

In some embodiments, the diaper 1 may also include a pair of ears (not shown) that extend from the side edges 32 of the diaper 1 into one of the waist regions. The ears may be integrally formed with a selected diaper component. For example, the ears may be integrally formed with the outer cover 17 or from the material employed to provide the top surface. In alternative configurations, the ears may be provided by members connected and assembled to the outer cover 17, the top surface, between the outer cover 17 and top surface, or in various other configurations.

As representatively illustrated in FIG. 2, the diaper 1 may also include a pair of containment flaps 12 that are configured to provide a barrier and to contain the lateral flow of body exudates. The containment flaps 12 may be located along the laterally opposed side edges 32 of the bodyside liner 5 adjacent the side edges of the absorbent core 3. The containment flaps 12 may extend longitudinally along the entire length of the absorbent core 3, or may only extend partially along the length of the absorbent core 3. When the containment flaps 12 are shorter in length than the absorbent core 3, they may be selectively positioned anywhere along the side edges 32 of diaper 1 in a crotch region 10. In one embodiment, the containment flaps 12 extend along the entire length of the absorbent core 3 to better contain the body exudates. Such containment flaps 12 are generally well known to those skilled in the art. For example, suitable constructions and arrangements for the containment flaps 12 are described in U.S. Pat. No. 4,704,116 to Enloe, which is incorporated herein in its entirety by reference thereto for all purposes.

The diaper 1 may include various elastic or stretchable materials, such as a pair of leg elastic members 6 affixed to the side edges 32 to further prevent leakage of body exudates and to support the absorbent core 3. In addition, a pair of waist elastic members 8 may be affixed to longitudinally opposed waist edges 15 of the diaper 1. The leg elastic members 6 and the waist elastic members 8 are generally adapted to closely fit about the legs and waist of the wearer in use to maintain a positive, contacting relationship with the wearer and to effectively reduce or eliminate the leakage of body exudates from the diaper 1. As used herein, the terms "elastic" and "stretchable" include any material that may be stretched and return to its original shape when relaxed. Suitable polymers for forming such materials include, but are not limited to, block copolymers of polystyrene, polyisoprene and polybutadiene; copolymers of ethylene, natural rubbers and urethanes; etc. Particularly suitable are styrene-butadiene block copolymers sold by Kraton Polymers of Houston, Tex. under the trade name Kraton®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Also suitable are coextruded composites of the foregoing, and elastomeric staple integrated composites where staple fibers of polypropylene, polyester, cotton and other materials are integrated into an elastomeric meltblown web. Certain elastomeric single-site or metallocene-catalyzed olefin polymers and copolymers are also suitable for the side panels.

The diaper 1 may also include one or more fasteners 30. For example, two flexible fasteners 30 are illustrated in FIG. 2 on opposite side edges of waist regions to create a waist opening and a pair of leg openings about the wearer. The shape of the fasteners 30 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 30 includes a separate piece of hook material affixed to the inside surface of a flexible backing.

The various regions and/or components of the diaper 1 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover 17 and bodyside liner 5 are assembled to each other and to the absorbent core 3 using an adhesive. Alternatively, the absorbent core 3 may be connected to the outer cover 17 using conventional fasteners, such as buttons, hook and loop type fasteners, adhesive tape fasteners, and so forth. Similarly, other diaper components, such as the leg elastic members 6, waist elastic members 8 and fasteners 30, may also be assembled into the diaper 1 using any attachment mechanism.

Although various configurations of a diaper have been described above, it should be understood that other diaper and absorbent article configurations are also included within the scope of the present invention. For instance, other suitable diaper configurations are described in U.S. Pat. Nos. 4,798,603 to Meyer et al.; 5,176,668 to Bemardin; 5,176,672 to Bruemmer et al.; 5,192,606 to Proxmire et al.; and 5,509,915 to Hanson et al., as well as U.S. Patent Application Pub. No. 2003/120253 to Wentzel, et al., all of which are incorporated herein in their entirety by reference thereto for all purposes. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Several examples of such absorbent articles are described in U.S. Pat. Nos. 5,197,959 to Buell; 5,085,654 to Buell; 5,634,916 to Lavon, et al.; 5,569,234 to Buell, et al.; 5,716,349 to Taylor, et al.; 4,950,264 to Osborn, III; 5,009,653 to Osborn, III; 5,509,914 to Osborn, III; 5,649,916 to DiPalma, et al.; 5,267,992 to Van Tillburg; 4,687,478 to Van Tillburq; 4,285,343 to McNair; 4,608,047 to Mattingly; 5,342,342 to Kitaoka; 5,190,563 to Herron, et al.; 5,702,378 to Widlund, et al.; 5,308,346 to Sneller, et al.; 6,110,158 to Kielpikowski; 6,663,611 to Blaney, et al.; and WO 99/00093 to Patterson, et al., which are incorporated herein in their entirety by reference thereto for all purposes. Still other suitable articles are described in U.S. Patent Application Publication No. 2004/0060112 A1 to Fell et al., as well as U.S. Pat. Nos. 4,886,512 to Damico et al.; 5,558,659 to Sherrod et al.; 6,888,044 to Fell et al.; and 6,511,465 to Freiburger et al., all of which are incorporated herein in their entirety by reference thereto for all purposes. The odor control particles may also be placed on fibers that are formed into a wet formed absorbent composite as described in U.S. Pat. No. 6,706,945 to Melius et al. Further, the odor control particles may also be incorporated into elastomeric absorbent composites, such as those described in U.S. Pat. No. 6,582,413 to Krautkramer, et al., which is incorporated herein in its entirety by reference thereto for all purposes.

The effectiveness of the odor control particles of the present invention may be measured in a variety of ways. For example, the percent of a malodorous compound adsorbed by the odor control particles may be determined in accordance with the headspace gas chromatography test set forth herein. In some embodiments, the odor control particles of the present invention are capable of adsorbing at least about 1%, in some embodiments at least about 2%, and in some embodiments, at least about 5% of a particular malodorous compound, such as mercaptans (e.g., ethyl mercaptan), ammonia, amines (e.g., trimethylamine (TMA), triethylamine (TEA), etc.), sulfides (e.g., hydrogen sulfide, dimethyl disulfide (DMDS), etc.), ketones (e.g., 2-butanone, 2-pentanone, 4-heptanone, etc.) carboxylic acids (e.g., isovaleric acid, acetic acid, propionic acid, etc.), aldehydes, terpenoids, hexanol, heptanal, pyridine, and so forth. It should be recognized that the surface chemistry of any one type of odor control particles may not be suitable to reduce all types of malodorous compounds, and that low adsorption of one or more malodorous compounds may be compensated by good adsorption of other malodorous compounds.

The present invention may be better understood with reference to the following examples.

Test Methods

Quantitative and qualitative odor tests were used in the Examples. Quantitative odor adsorption was determined in the Examples using a test known as "Headspace Gas Chromatography." Headspace gas chromatography testing was conducted on an Agilent Technologies 5890, Series II gas chromatograph with an Agilent Technology 7694 headspace sampler (Agilent Technologies, Waldbronn, Germany). Helium was used as the carrier gas (injection port pressure: 87.5 kPa; headspace vial pressure: 108.9 kPa; supply line pressure is at 413.4 kPa). A DB-624 column was used for the malodorous compound that had a length of 30 meters and an internal diameter of 0.25 millimeters. Such a column is available from J&W Scientific, Inc. of Folsom, Calif.

The operating parameters used for the headspace gas chromatography are shown below in Table 1:

TABLE 1

| Operating Parameters for the Headspace Gas Chromatography Device. Headspace Parameters | | |
|---|---|---|
| Zone Temps, ° C. | Oven | 37 |
| | Loop | 85 |
| | TR. Line | 90 |
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing approximately 5 milligrams of the odor control agent in a 22.1-cubic centimeter headspace vial. Using a syringe, an aliquot of the malodorous compound was also placed in the vial. Testing was done with 2.014 micrograms of ethyl mercaptan (2.4 microliters) and 2.178 micrograms (3 microliters) of triethylamine (TEA). Each sample was tested in triplicate. The vial was then sealed with a cap and a septum and placed in the headspace gas chromatography oven at 37° C. After two (2) hours, a hollow needle was inserted through the septum and into the vial. A 1-cubic centimeter sample of the headspace (air inside the vial) was then injected into the gas chromatograph. Initially, a control vial with only the aliquot of malodorous compound was tested to define 0% malodorous compound adsorption. To calculate the amount of headspace malodorous compound removed by the sample, the peak area for the malodorous compound from the vial with the sample was compared to the peak area from the malodorous compound control vial.

Qualitative odor reduction was also assessed against urine odor.

EXAMPLE 1

Modified silica particles were prepared for treatment of a pulpsheet. The silica particles were Snowtex-OXS, which are colloidal silica nanoparticles commercially available from Nissan Chemical America of Houston, Tex. The particles have an average particle size of between 4 to 6 nanometers and a surface area between 200 to 500 square meters per gram as measured using the BET (Brunauer, Emmett and Teller) method. The silica particles were modified with a transition metal as follows. A solution of Snowtex-OXS (324 grams $SiO_2$, $3.62 \times 10^{-3}$ moles $SiO_2$ particle, about 3 liters of Snowtex-OXS stock solution) was diluted with a solution of $NaHCO_3$ (13.44 grams $NaHCO_3$ in 500 milliliters water, 0.04 molar final concentration for 4 liters) until the pH was about 8. A solution of iron (III) chloride hexahydrate ($FeCl_3 \cdot 6H_2O$) (97.9 grams, 0.362 moles) in water (500 milliliters) was added to the Snowtex-OXS solution via an addition funnel with vigorous stirring. The final silica concentration was 7.5% wt/wt. The iron-coated silica particle solution turned light orange after the addition of the metal salt and was stirred at room temperature for 2 hours.

EXAMPLE 2

NB-416 southern softwood pulpsheet (available from Weyerhaeuser Co. of Federal Way, Wash.) was treated with the particle solution of Example 1. Specifically, the solution was sprayed onto both sides of NB-416 pulpsheet to attain 45.9 milligrams iron-coated silica particles per gram of pulp. The treated pulpsheet was dried at 50° C. overnight. The treated pulpsheet was then fiberized using a Kamas Laboratory Hammermill, Model H-01 pulp fiberizer to form fluff pulp.

EXAMPLE 3

Modified silica particles were prepared for treatment of a superabsorbent material. The silica particles were Snowtex-OXS, which are colloidal silica nanoparticles commercially available from Nissan Chemical America of Houston, Tex. The particles have an average particle size of between 4 to 6 nanometers and a surface area between 200 to 500 square meters per gram. The silica particles were modified with a transition metal as follows. A solution of Snowtex-OXS (216 grams $SiO_2$, $2.41 \times 10^{-3}$ moles $SiO_2$ particle, ~2 liters of Snowtex-OXS stock solution) was diluted with a solution of $NaHCO_3$ (13.44 g NaHCO3 in 1 liter, 0.04 molar final concentration for 4 liters) until the pH was about 8. A solution of iron (III) chloride hexahydrate ($FeCl_3 \cdot 6H_2O$) (65.25 grams, 0.241 moles) in water (1 liter) was added to the OXS solution via an addition funnel with vigorous stirring. The final silica concentration was 5% wt/wt. The iron coated silica particle solution turned light orange after the addition of the metal salt and stirred at room temperature for 2 hours.

EXAMPLE 4

Hysorb® 8800AD superabsorbent (available from BASF of Charlotte, N.C.) was treated with the particle solution of Example 3. Specifically, six hundred (600) grams of the solution was added to a one gallon Hobart® mixer, Model N50, manufactured by Hobart Canada of Ontario, Canada. One hundred fifty (150) grams of distilled water was then added to the mixer. The mixer was stirred at a slow speed (setting 1). Five hundred (500) grams dry Hysorb® 8800AD superabsorbent particles were added to the mixer while stirring. After stirring for about 30 seconds, the swollen superabsorbent was discharged into a stainless steel pan (25.4 cm×50.8 cm or 10 inches×20 inches). The treated superabsorbent was then dried in an oven at 60° C. for three days to attain 60 milligrams of iron-coated silica particles per gram of superabsorbent. Non-agglomerated treated superabsorbent particles were separated for testing by sieving to attain particle sizes of 150 microns to 850 microns.

EXAMPLE 5

Hysorb® 8800AD superabsorbent (available from BASF of Charlotte, N.C.) was treated with the particle solution of Example 3. Specifically, four hundred sixty (460) grams of the solution was added to a one gallon Hobart® mixer. Two hundred ninety (290) grams of distilled water was added to the mixer. The mixer was stirred at a slow speed (setting 1). Five hundred (500) grams dry Hysorb® 8800AD superabsorbent particles were added to the mixer while the stirrer was on. After stirring for about 30 seconds, the swollen superabsorbent was discharged into a stainless steel pan (25.4 cm×50.8 cm or 10 inches×20 inches). The treated superabsorbent was dried in an oven at 60° C. for three days to attain 45.9 milligrams iron coated silica particles per gram of superabsorbent. Non-agglomerated treated superabsorbent particles were separated for testing by sieving to attain particle sizes of 150 microns to 850 microns.

EXAMPLE 6

Weyerhaeuser NB-416 pulpsheet was treated with Acid Green 25, an anthraquinone-based Drug & Cosmetic approved dye available from Sigma-Aldrich of St. Louis, Mo. To form the Acid Green 25 solution, water (4 liters) was added to a 4 liter bottle, after which Acid Green 25 (40 grams, 0.0642 moles) was added. The final Acid Green 25 concentration was 1% wt/wt. Acid Green 25 solution was sprayed onto both sides of NB-416 pulpsheet to attain 16.5 milligrams Acid Green 25 per gram of pulp. The treated pulpsheet was dried at 50° C. overnight. The treated pulpsheet was then fiberized using a Kamas Laboratory Hammermill, Model H-01 pulp fiberizer to form fluff pulp.

EXAMPLE 7

Modified silica particles were prepared. The silica particles were Snowtex-AK, which are colloidal silica nanoparticles commercially available from Nissan Chemical America of Houston, Tex. The particles have an average particle size of between 10 to 20 nanometers and a surface area between 200 to 500 square meters per gram. The silica particles were modified with Acid Green 25 as follows. Water (3.733 liters) was added to a 4 liter bottle, after which Acid Green 25 (40 grams) was added. The solution was shaken vigorously to affect dissolution, followed by addition of Snowtex-AK particles (267 ml, ~15 wt % in water initially) to generate a final solution concentration of 1% wt/wt Snowtex-AK.

EXAMPLE 8

Weyerhaeuser NB-416 pulpsheet was treated with the solution of Example 7 by spraying it onto both sides of the pulpsheet to attain 29.4 milligrams Acid Green 25 coated silica particles per gram of pulp. The treated pulpsheet was dried at 50° C. overnight. The treated pulpsheet was then fiberized using a Kamas Laboratory Hammermill, Model H-01 pulp fiberizer to form fluff pulp.

Example 9

The effectiveness of the treated pulpsheet and superabsorbent to adsorb malodorous compounds was demonstrated. The materials of Examples 2, 4, 5, 6, and 8 were tested for odor adsorption as described above. For comparative purposes, untreated fiberized NB-416 fluff pulp and Hysorb 8800AD superabsorbent were also tested. The results are set forth below in Tables 2 and 3 in terms of milligrams of the malodorous compound removed per gram of sample, i.e., relative adsorption efficiency.

TABLE 2

Removal of Triethylamine

| Sample | Relative Adsorption Efficiency |
|---|---|
| Hysorb ® 8800AD | −0.40 |
| Iron/OXS treated Hysorb ® 8800AD from Ex. 4 | 3.80 |
| Iron/OXS treated Hysorb ® 8800AD from Ex. 5 | 3.00 |
| NB-416 fluff pulp | 0.74 |
| Iron/OXS treated NB-416 from Ex. 2 | 15.20 |
| Acid Green 25 treated NB-416 from Ex. 6 | 1.10 |
| AG 25/AK treated NB-416 from Ex. 8 | 2.30 |

TABLE 3

Removal of Ethyl Mercaptan

| Sample | Relative Adsorption Efficiency |
|---|---|
| Hysorb ® 8800AD | −0.80 |
| Iron/OXS treated Hysorb ® 8800AD from Ex. 4 | 0.20 |
| Iron/OXS treated Hysorb ® 8800AD from Ex. 5 | −0.10 |
| NB-416 fluff pulp | 0.58 |
| Iron/OXS treated NB-416 from Ex. 2 | 1.30 |
| Acid Green 25 treated NB-416 from Ex. 6 | 0.20 |
| AG 25/AK treated NB-416 from Ex. 8 | 1.50 |

As indicated, improved odor control was observed in comparison with untreated pulp and superabsorbent materials. The effect was stronger with triethylamine than with ethyl mercaptan.

EXAMPLE 10

Fluff pulp and superabsorbent were homogeneously air-formed into absorbent composites. The formed absorbent composites were then compressed using a Beloit Wheeler Model 700 debulking unit. The materials produced are shown below in Table 4.

TABLE 4

Airformed Absorbent Composites

| Pulp type | Superabsorbent | Superabsorbent % | Pulp g/m$^2$ | Superabsorbent g/m$^2$ | Density (g/cm$^3$) |
|---|---|---|---|---|---|
| NB-416 | Hysorb ® 8800AD | 27 | 398 | 147 | 0.12 |
| NB-416 | Hysorb ® 8800AD | 50 | 193 | 193 | 0.24 |
| NB-416 | Iron/OXS treated Hysorb ® 8800AD from Ex. 4 | 27 | 398 | 147 | 0.12 |
| NB-416 | Iron/OXS treated Hysorb ® 8800AD from Ex. 5 | 50 | 193 | 193 | 0.24 |
| Treated NB-416 from Ex. 2 | Hysorb ® 8800AD | 50 | 193 | 193 | 0.24 |
| Treated NB-416 from Ex. 8 | Hysorb ® 8800AD | 50 | 193 | 193 | 0.24 |

EXAMPLE 11

The effectiveness of the treated pulpsheet and superabsorbent to adsorb malodorous compounds when converted into an air-formed absorbent composite was demonstrated. The materials of Example 10 were tested for odor adsorption as described above. The results are set forth in Tables 5 and 6 in terms of milligrams of the malodorous compound removed per gram of sample, i.e., relative adsorption efficiency.

TABLE 5

Removal of Triethylamine

| Pulp type | Superabsorbent | Superabsorbent % | Relative Adsorption Efficiency |
|---|---|---|---|
| NB-416 | Hysorb ® 8800AD | 27 | 1.21 |
| NB-416 | Hysorb ® 8800AD | 50 | 1.11 |
| NB-416 | Iron/OXS treated Hysorb ® 8800AD from Ex. 4 | 27 | 2.94 |
| NB-416 | Iron/OXS treated Hysorb ® 8800AD from Ex. 5 | 50 | 2.70 |
| Iron/OXS treated NB-416 from Ex. 2 | Hysorb ® 8800AD | 50 | 4.12 |
| AG 25/AK treated NB-416 from Ex. 8 | Hysorb ® 8800AD | 50 | 1.73 |

TABLE 6

Removal of Ethyl Mercaptan

| Pulp type | Superabsorbent | Superabsorbent % | Relative Adsorption Efficiency |
|---|---|---|---|
| NB-416 | Hysorb ® 8800AD | 27 | 0.12 |
| NB-416 | Hysorb ® 8800AD | 50 | −0.05 |
| NB-416 | Iron/OXS treated Hysorb ® 8800AD from Ex. 4 | 27 | 0.13 |
| NB-416 | Iron/OXS treated Hysorb ® 8800AD from Ex. 5 | 50 | 0.06 |
| Iron/OXS treated NB-416 from Ex. 2 | Hysorb ® 8800AD | 50 | 0.25 |
| AG 25/AK treated NB-416 from Ex. 8 | Hysorb ® 8800AD | 50 | 0.05 |

As indicated, improved odor control was observed in comparison with untreated pulp and superabsorbent materials.

EXAMPLE 12

To determine the potential for urine odor reduction, 76 mm (3 inch) diameter circles of the absorbent composites of Example 10 were insulted with 10 milliliters of pooled female urine that had been incubated at 37° C. for 6 hours and then filtered using a polyethersulfone (PES) membrane available from Corning of Acton, Mass. The materials were then incubated at 37° C. for 1 hour in 1-qt screw top mason jars before assessment. Four panelists rated the pads on a scale of 1 to 10 for urine odor, with lower numbers signifying low urine odor and high numbers signifying high urine odor. The results are shown below in Table 7.

TABLE 7

Urine Odor Control Rankings

| Pulp type | Super-absorbent | Super-absorbent % | Panelist 1 | Panelist 2 | Panelist 3 | Panelist 4 |
|---|---|---|---|---|---|---|
| NB-416 | Hysorb ® 8800AD | 27 | 9 | 8 | 10 | 8 |
| NB-416 | Hysorb 8800AD | 50 | 10 | 8 | 7 | 7 |
| NB-416 | Iron/OXS treated Hysorb ® 8800AD from Ex. 4 | 27 | 4 | 8 | 5 | 1 |
| NB-416 | Iron/OXS treated Hysorb ® 8800AD from Ex. 5 | 50 | 4 | 8 | 3 | 2 |
| Treated NB-416 from Ex. 2 | Hysorb ® 8800AD | 50 | 1 | 1 | 1 | 2 |
| Treated NB-416 from Ex. 8 | Hysorb ® 8800AD | 50 | 5 | 10 | 3 | 10 |

As indicated, decreased urine odor was observed in comparison with untreated pulp and superabsorbent materials.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article having odor control properties, the article comprising an absorbent core that includes an airformed web, the airformed web containing a matrix of fluff pulp fibers in which odor control particles are homogeneously distributed throughout the matrix by binding along lengths of fibers used to form the matrix prior to formation of the matrix, wherein the binding is accomplished without the use of chemical binders or other attachment structures, wherein the pulp fibers are separated via fiberizing after odor control particle binding and the separated fibers then form the matrix, wherein the odor control particles are inorganic oxide particles, wherein the inorganic oxide particles have an average particle size of from about 1 nanometer to about 50 nanometers.

2. The absorbent article of claim 1, wherein the inorganic oxide particles contain silica, alumina, or both.

3. The absorbent article of claim 1, wherein the inorganic oxide particles are modified with a transition metal.

4. The absorbent article of claim 1, wherein the odor control particles are present in an amount of from about 0.01 to about 20 wt. % of the airformed web.

5. The absorbent article of claim 1, wherein the odor control particles are present in an amount of from about 0.1 to about 10 wt. % of the airformed web.

6. The absorbent article of claim 1, wherein the absorbent core consists essentially of the airformed web.

7. The absorbent article of claim 1, wherein the article is an incontinent article.

8. The absorbent article of claim 1, wherein the article is a diaper.

9. An absorbent article having odor control properties, the article comprising an absorbent core that includes an airformed web, the airformed web containing a matrix of fluff pulp fibers in which odor control particles are homogeneously distributed throughout the matrix by binding along lengths of fibers used to form the matrix prior to formation of the matrix, wherein the binding is accomplished without the use of chemical binders or other attachment structures, wherein the pulp fibers are separated via fiberizing after odor control particle binding and the separated fibers then form the matrix, wherein the odor control particles contain an odor control agent applied to carrier particles, wherein the odor control agent contains inorganic oxide particles, wherein the inorganic particles have an average particle size of from about 1 nanometer to about 50 nanometers.

10. The absorbent article of claim 9, wherein the carrier particles are superabsorbent particles.

11. The absorbent article of claim 10, wherein the odor control agent is coated onto the superabsorbent particles.

12. The absorbent article of claim 9, wherein the odor control particles are present in an amount of from about 0.01 to about 20 wt. % of the airformed web.

13. The absorbent article of claim 9, wherein the odor control particles are present in an amount of from about 0.1 to about 10 wt. % of the airformed web.

14. The absorbent article of claim 9, wherein the absorbent core consists essentially of the airformed web.

15. The absorbent article of claim 9, wherein the article is an incontinent article.

16. The absorbent article of claim 9, wherein the article is a diaper.

* * * * *